United States Patent
Balagurusamy et al.

(10) Patent No.: US 10,031,065 B2
(45) Date of Patent: Jul. 24, 2018

(54) DETECTION OF PATHOGENS AND ALLERGENS

(71) Applicant: INTERNATIONAL BUSINESS MACHINES CORPORATION, Armonk, NY (US)

(72) Inventors: Venkat K. Balagurusamy, Suffern, NY (US); Stephen J. Heisig, Tarrytown, NY (US); Joseph W. Ligman, Wilton, CT (US); Gong Su, New York, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 106 days.

(21) Appl. No.: 15/099,929

(22) Filed: Apr. 15, 2016

(65) Prior Publication Data
US 2017/0299496 A1   Oct. 19, 2017

(51) Int. Cl.
*G06K 9/00*  (2006.01)
*G01N 15/14*  (2006.01)
(Continued)

(52) U.S. Cl.
CPC ..... *G01N 15/1463* (2013.01); *G01N 15/1429* (2013.01); *G01N 33/483* (2013.01);
(Continued)

(58) Field of Classification Search
CPC ........ G01N 15/1463; G01N 2015/0065; G06T 7/2033; G06T 2207/10016; G06T 2207/10056; G06T 2207/30072
See application file for complete search history.

(56) References Cited

U.S. PATENT DOCUMENTS

| | | | | |
|---|---|---|---|---|
| 2003/0215844 | A1* | 11/2003 | Chapsky | B82Y 5/00 435/6.16 |
| 2005/0123937 | A1* | 6/2005 | Thorp | B82Y 15/00 435/6.12 |

(Continued)

OTHER PUBLICATIONS

U.S. Appl. No. 14/725,668; "Cellular Phone Based Optical Detection of Specific Nucleic Acid Sequences"; filed May 29, 2015.

*Primary Examiner* — Bhavesh Mehta
*Assistant Examiner* — Ian Lemieux
(74) *Attorney, Agent, or Firm* — Cantor Colburn LLP; Rabin Bhattacharya (57) ABSTRACT

Embodiments include methods, systems and computer program products for communicating the presence of a target DNA or RNA sequence. Aspects include receiving a plurality of images of a sample taken by a portable video capture device. Aspects also include calculating a change in position over time of microscopic beads coated with DNA probe sequence in a sample containing genetic material. Aspects also include determining whether the beads are displaying Brownian motion. Aspects also include, based upon a determination of that the beads are displaying Brownian motion, generating a negative output message and sending the negative output message to a portable display. Aspects also include, based upon a determination of that the beads are not displaying Brownian motion, generating a positive output message and sending the positive output message to a portable display.

20 Claims, 6 Drawing Sheets

(51) Int. Cl.
*G06T 7/20* (2017.01)
*G01N 33/483* (2006.01)
*G01N 15/10* (2006.01)

(52) U.S. Cl.
CPC .... *G06T 7/2033* (2013.01); *G01N 2015/1006* (2013.01); *G01N 2015/1488* (2013.01); *G06T 2207/10016* (2013.01); *G06T 2207/10056* (2013.01); *G06T 2207/30072* (2013.01)

(56) References Cited

U.S. PATENT DOCUMENTS

| | | | |
|---|---|---|---|
| 2009/0238423 A1* | 9/2009 | Rigler | G01N 35/00871 382/128 |
| 2009/0253181 A1* | 10/2009 | Vangbo | G01N 27/44791 435/91.1 |
| 2011/0160090 A1* | 6/2011 | Cary | C12Q 1/6823 506/16 |
| 2015/0307926 A1* | 10/2015 | Celedon | C12Q 1/6825 435/5 |

* cited by examiner

DETECTION OF PATHOGENS AND ALLERGENS

BACKGROUND

The present disclosure relates generally to detection of pathogens and allergens using portable devices, and more specifically to methods, systems and computer program products for communication of the presence of target nucleic acid sequences.

Detection of target nucleic acid sequences, such as DNA and RNA sequences can aid with identification of pathogens and allergens in a sample material. A nucleic acid sequence is typically represented by a succession of letters that indicate the order of nucleotides within a deoxyribonucleic acid (DNA) (using G, A, C, and T) or ribonucleic (RNA) (G, A, C and U) molecule. By convention, sequences are usually presented from the 5' end to the 3' end.

Deoxyribonucleic acid (DNA) is a molecule that encodes the genetic instructions used in the development and functioning of all known living organisms and viruses. Ribonucleic acid (RNA) is a polymeric molecule. It is implicated in various biological roles in coding, decoding, regulation, and expression of genes.

SUMMARY

In accordance with an embodiment, a computer-implemented method for communicating the presence of a target DNA or RNA sequence is provided. The method includes receiving a plurality of images of a sample solution taken by a portable video capture device, wherein each of the images is an image of the sample solution at a unique time, and wherein the sample solution contains a plurality of microscopic beads comprising a DNA probe sequence and a genetic material sample. The method also includes calculating a change in position of each of the microscopic beads over time based upon the plurality of images. The method also includes determining, based upon the calculated changes in position, whether the plurality of microscopic beads are displaying Brownian motion. The method also includes, responsive to a determination that the plurality of microscopic beads are displaying Brownian motion, generating a negative output message and sending the negative output message to a portable display. The method also includes, responsive to a determination that the plurality of microscopic beads are not displaying Brownian motion, generating a positive output message and sending the positive output message to the portable display.

In accordance with another embodiment, a computer program product for communicating the presence of a target DNA or RNA sequence is provided. The computer program product includes a computer readable storage medium having program instructions embodied therewith, the program instructions executable by a processor to cause the processor receive a plurality of images of a sample solution taken by a portable video capture device, wherein each of the images is an image of the sample solution at a unique time, and wherein the sample solution comprises a plurality of microscopic beads comprising a DNA probe sequence and a genetic material sample. The processor is also configured to calculate a change in position of each of the microscopic beads over time based upon the plurality of images. The processor is also configured to determine, based upon the calculated changes in position, whether the plurality of microscopic beads are displaying Brownian motion. The processor is also configured to, responsive to a determination that the plurality of microscopic beads are displaying Brownian motion, generate a negative output message and send the negative output message to a portable display. The processor is also configured to, responsive to a determination that the plurality of microscopic beads are not displaying Brownian motion, generate a positive output message and send the positive output message to the portable display.

In accordance with a further embodiment, a processing system for communicating the presence of a target DNA or RNA sequence includes a portable video capture device, a portable display, and processor in communication with one or more types of memory. The processor is configured to receive a plurality of images of a sample solution taken by the portable video capture device, wherein each of the images is an image of the sample solution at a unique time, and wherein the sample solution comprises a plurality of microscopic beads comprising a DNA probe sequence and a genetic material sample. The processor is also configured to calculate a change in position of each of the microscopic beads over time based upon the plurality of images. The processor is also configured to determine, based upon the calculated changes in position, whether the plurality of microscopic beads are displaying Brownian motion. The processor is also configured to, responsive to a determination that the plurality of microscopic beads are displaying Brownian motion, generate a negative output message and send the negative output message to the portable display. The processor is also configured to, responsive to a determination that the plurality of microscopic beads are not displaying Brownian motion, generate a positive output message and send the positive output message to the portable display.

BRIEF DESCRIPTION OF THE DRAWINGS

The subject matter of the present disclosure is particularly pointed out and distinctly claimed in the claims at the conclusion of the specification. The foregoing and other features and advantages of the one or more embodiments disclosed herein are apparent from the following detailed description taken in conjunction with the accompanying drawings in which:

DETAILED DESCRIPTION

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 1:
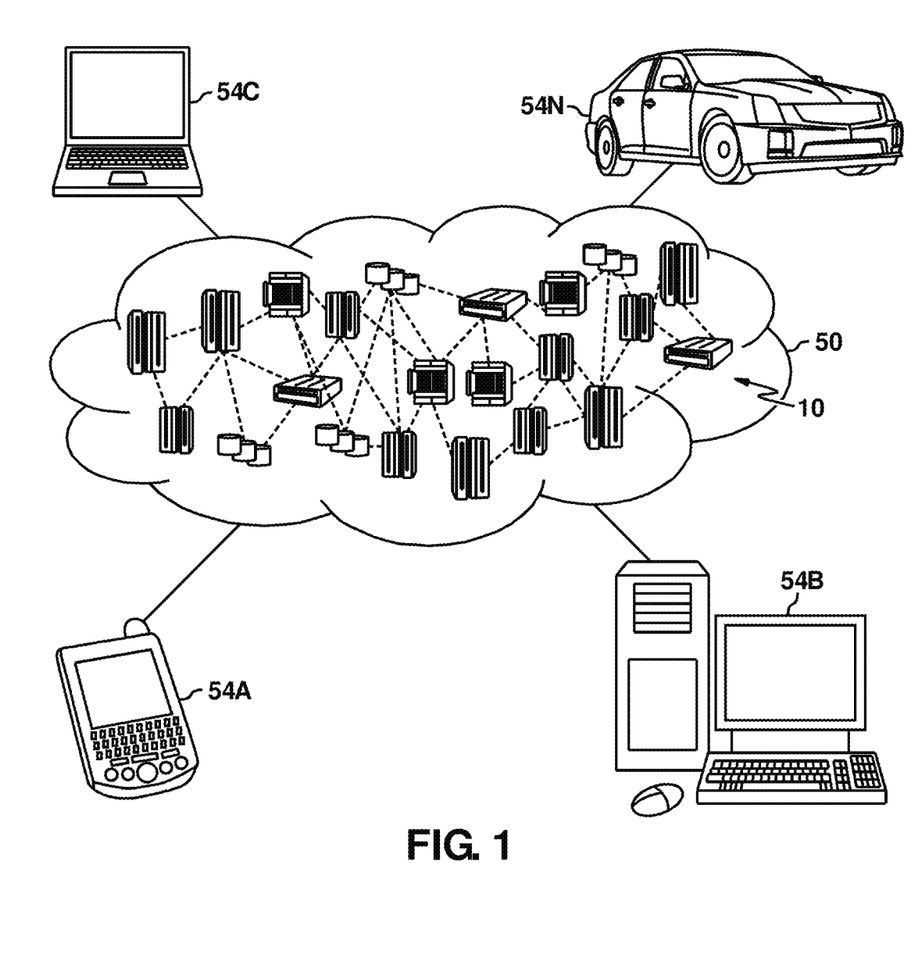
FIG. 1 depicts a cloud computing environment according to one or more embodiments of the present invention.

Referring now to FIG. 1, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
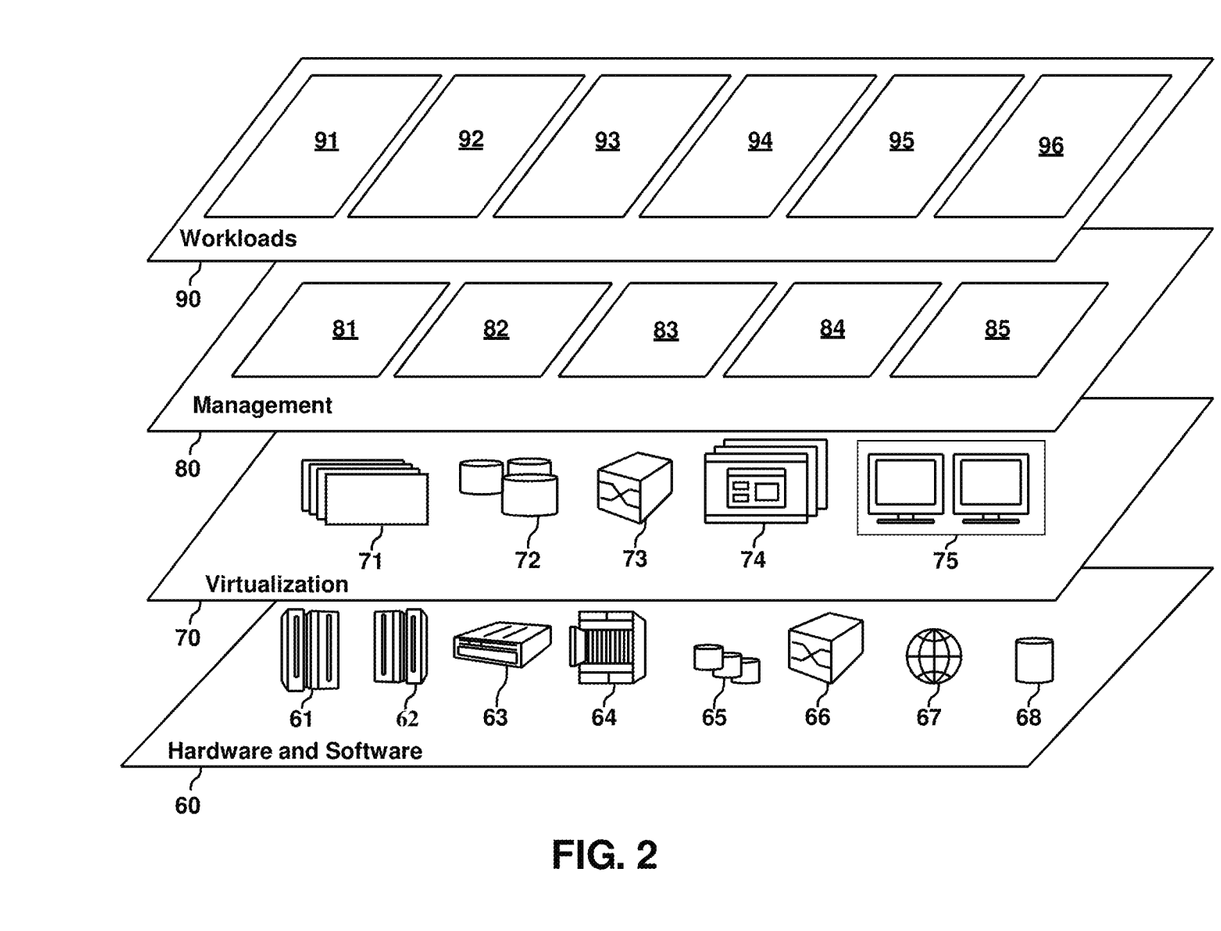
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and image processing 96.

Figure 3:
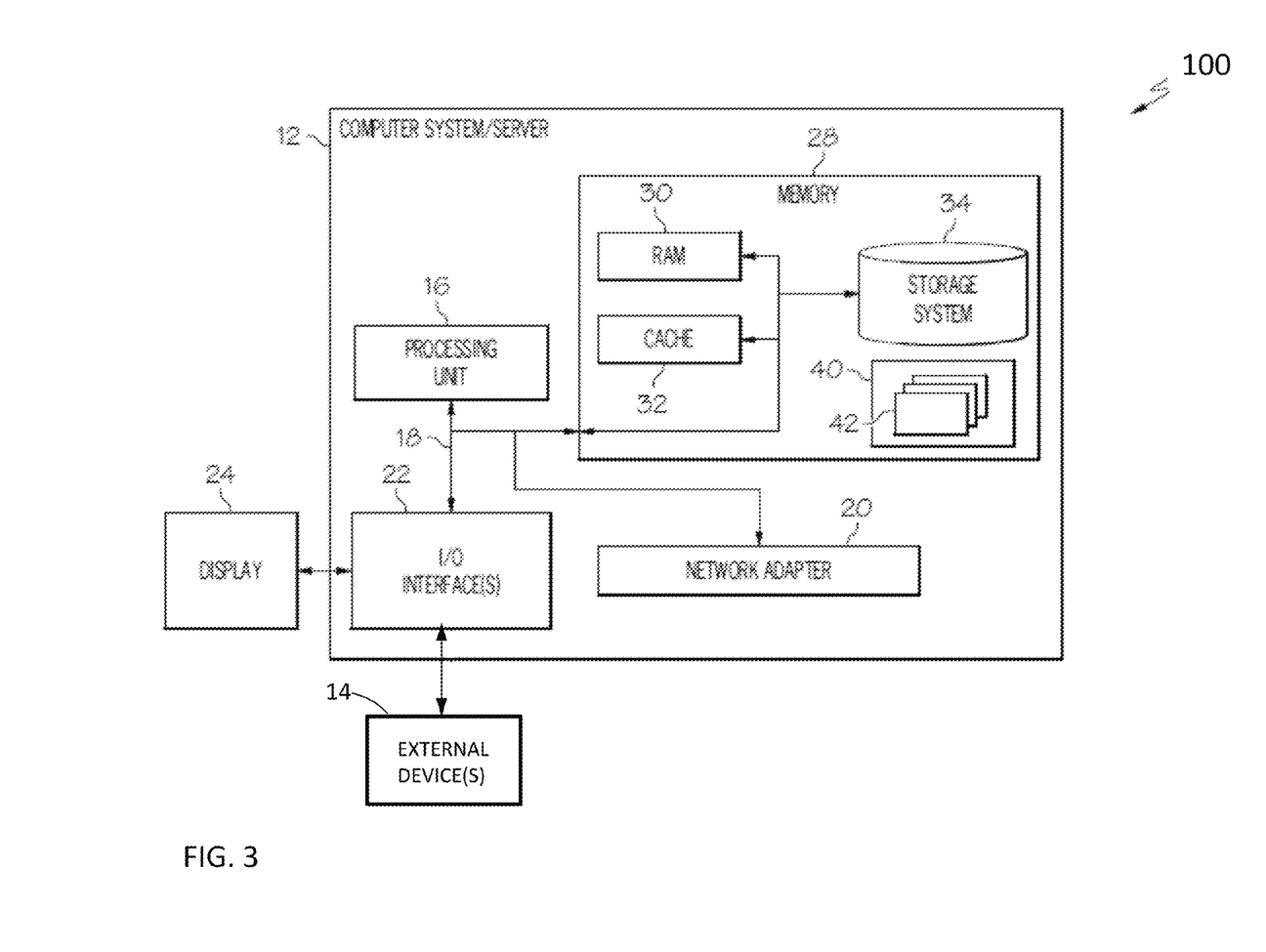
FIG. 3 is a computer system according to one or more embodiments.

Referring now to FIG. 3, a schematic of a cloud computing node 100 included in a distributed cloud environment or cloud service network is shown according to a non-limiting embodiment. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 in cloud computing node 100 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of the present disclosure, one or more embodiments provide systems and methodologies for communicating the presence of a DNA or RNA sequence in a sample solution. More specifically, the present disclosure provides portable detection and analysis of allergens and pathogens with readily available consumer devices.

There are times when one needs to know whether a sample, which may be any item or substance being tested, contains a known nucleic acid sequence. Despite various food labelling regulations, the possibility still exists that products may be inadvertently, or even intentionally, mislabeled. For example, Europe and the U.S. have begun requiring labelling of genetically modified (GM) food. Because the possibility of inadvertent or intentional mislabeling exits, it is desirable to provide the capability to confirm whether a shipment of corn was actually from non-GM plants or GM plants. In another scenario, individuals with Celiac disease become sick if they eat gluten. Similarly, because the possibility of inadvertent or intentional mislabeling exists, it is desirable to provide the capability to confirm whether or not an allegedly "gluten-free" product really contains gluten.

Embodiments provide techniques to communicate the presence of a target DNA or RNA sequence in a sample solution. More specifically, embodiments provide systems, methods, and computer program products for communicating the presence of a target DNA or RNA sequence using a portable video capture device (e.g., a smart phone or the like). Accordingly, embodiments can communicate to a user of a portable device the presence of pathogens, viruses, organisms, and particular DNA and RNA molecules, etc., using portable devices, such as smart phones, tablets, or smart watches.

Detection of the restricted Brownian motion of microparticles, which can be applied to detect the genetic material (DNA/RNA) of flu and other viruses, bacteria, and other organisms, can provide information regarding the presence or absence of an organism. Where sample genetic material is immobilized on a surface and combined with a solution containing a DNA probe tethered to a microscopic bead, if the DNA probe associates with its target material, the movement of the microscopic bead will be restricted. If the DNA probe does not find a target material, on the other hand, the microscopic bead will move about in the solution through Brownian motion. Enabling such detection with a mobile device can broaden the applications in which such methods can be employed, for example allowing on-location analysis of surfaces for bacterial pathogens, identification of Ebola, or identification of HIV and other viruses. Moreover, in the food industry, there is a need for easy and portable identification of nucleic acid sequences specific to, for example, raw meats (e.g., sushi), gluten or genetically modified foods.

The disclosure provides portable video capture and analysis of DNA and RNA materials and methods of communicating the presence or absence of target sequences to a user. The disclosure also provides methods of storing, analyzing, and sharing collected data in a shared pool of configurable computing resources such as the cloud computing environment described herein. Using a cloud computing environment can expand the processing capabilities of systems and methods for identifying DNA and RNA target materials, potentially providing faster or more expansive analysis.

Smart phones and other portable devices are built with robust and high-resolution image capturing and processing capabilities, which are utilized in embodiments disclosed herein. There is a growing need for quick and easy diagnosis of flu-like symptoms with point-of-care diagnostic kits at one's home, away from the doctor's office, or at an epidemic center. This is also highlighted by the recent epidemic associated with the Ebola virus. There have been recent advances made by researchers in developing mobile-phone based sensing devices, for example, for flow cytometry analysis and polymerase chain reaction (PCR) based DNA detection. However, the present disclosure relates to techniques using the Brownian motion of microparticles to detect the presence of DNA or RNA molecules specific to a known DNA sequence such as, for example, the flu type virus.

Colloidal or polymer particles of micron size undergo random motion in a liquid (also referred to as a medium or solution), and this random motion is characteristic of the Brownian motion. Brownian motion can also be observed in air, for example, by watching small pollen grains or dust particles suspended in air shined by a beam of sun light. In both cases, the origin of their random motion can be explained by the random motion of the underlying much smaller molecules that make up either the air or liquid. As these small molecules constantly collide with the bigger particles embedded in them, at any moment there is imbalance in the net force imparted by these small molecules on the bigger particles. This imbalance in the net force results in the movement of the bigger particles and results in the net force being random in direction and magnitude. Therefore, the imbalance in the net force causes random movement of the bigger particles. It follows that in order for this random motion to be detectable macroscopically, for example, either with the naked eye or with a simple optical microscope, the size of the bigger particles cannot be too big compared to the size of the small molecules. The Brownian motion of particles in three dimensions is well described by a simple equation for mean-square displacement (MSD):

$$\delta x^2 = 6\ Dt$$

where t is time. The MSD used in Statistical mechanical description of particle motion is defined as:

$$\langle x(t)-x(0) \rangle^2$$

where x(t) represents the position of the particle at time t, x(0) initial position and the angled brackets represent time average. Supposing one knows the positions of a particle over a time duration at an interval δt, then MSD can be calculated from the equation:

$$\delta x^2 = [(x(t_1)-x(0))^2 + (x(t_2)-x(0))^2 + (x(t_3)-x(0))^2 + \ldots + (x(t_n)-x(0))^2]/n$$

Where n is the number of consecutive positions of the particle.

The only constant in this equation that characterizes the particle is the diffusion constant, D. The diffusion constant D can be calculated from Einstein's relation $$D = \mu k_B T$$

where $k_B$ is the Boltzmann constant, $\mu$ is the mobility of the diffusing particle, and T is the temperature of the medium (liquid) the particle is diffusing in.

For a spherical particle, the mobility can be calculated from Stokes law for the drag force on the particle and Einstein's relation simplifies to $$D = \frac{k_B T}{6\pi\eta r}$$

where 'r' is the radius of the particle, is the dynamic viscosity of the medium (liquid). In addition to the simple equation that can be used to calculate the diffusion coefficient D of the particle, experimentally measured values are also widely available for polymer micro-beads and DNA molecules. So given the temperature T and the nature of the medium (e.g., the dynamic viscosity η) in which the particle is present, the mean-square displacement ($\delta x^2$) of the particle can be calculated and will be linear in time duration of the observation of the particle.

Figure 4:
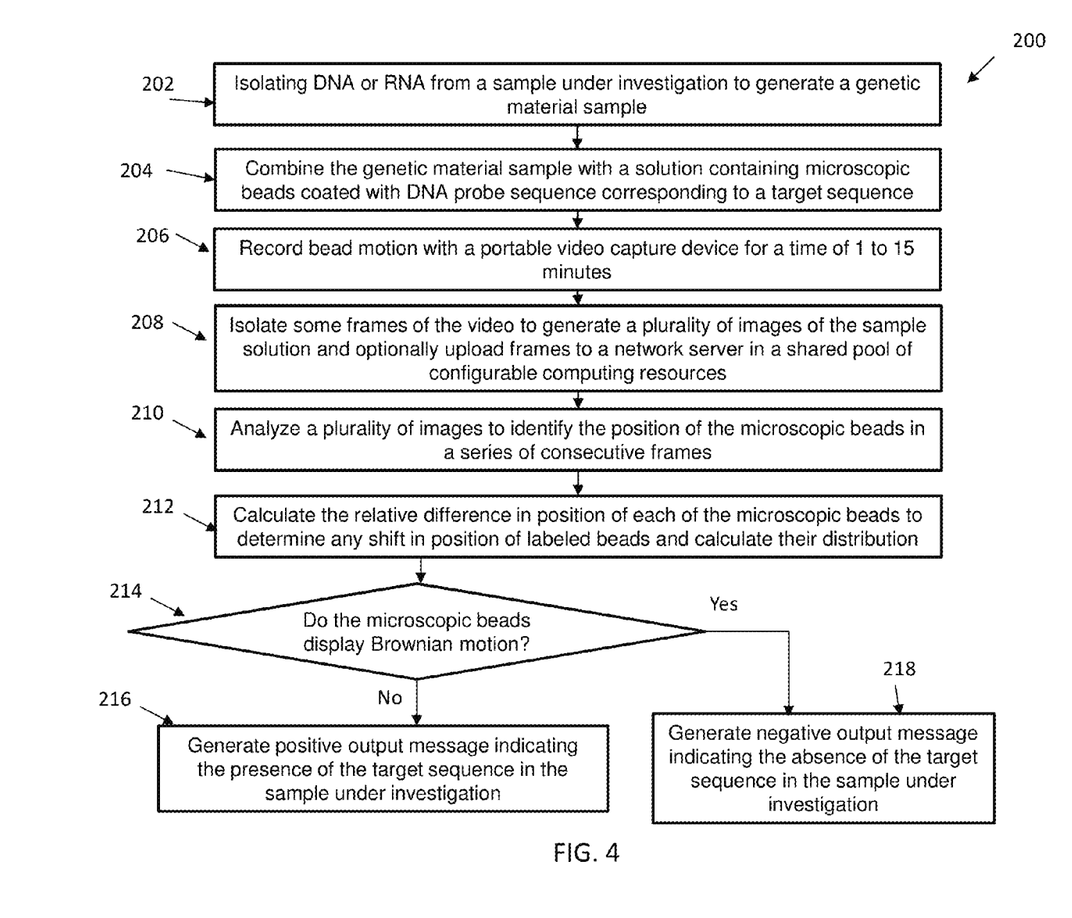
FIG. 4 is a flow diagram illustrating a method for communicating the presence of a target DNA or RNA sequence according to one or more embodiments.

Referring now to FIG. 4, a flow chart illustrating a method 200 for communicating the presence of a target DNA or RNA sequence using a portable video capture device. As shown at block 202, the method 200 includes isolating DNA or RNA from a sample under investigation to generate a genetic material sample. As shown at block 204, the method 200 includes combining the genetic material sample with a solution containing microscopic beads coated with DNA probe sequence corresponding to a target sequence. Methods of coating microscopic beads with probe DNA are known. In accordance with the disclosure, the genetic material sample contains DNA or RNA that is tethered to a surface. A solution containing microscopic beads coated with DNA probe sequence are added to the genetic material sample containing the tethered nucleic acid segments. DNA probe sequences are such that they are complimentary to a target nucleic acid sequence and therefore, when in proximity to the target sequence, can bind to the target sequence. Thereby, upon binding to a target, the microscopic beads coated to the now bound DNA probe sequence will no longer move through the solution with Brownian motion and, instead, will have constrained movement.

As shown at block 206, the method 200 includes recording bead motion with a portable video capture device. For example, the bead motion can be captured for a time of one to fifteen minutes. The method 200 also includes, as shown at block 208, isolating some frames of the video to generate a plurality of images of the sample solution. In some embodiments, images are subject to pre-processing, for example to convert images or filter noise from the images. Optionally, the frames can be uploaded to a network server in a shared pool of configurable computing resources. For instance, the frames can be uploaded to a cloud computing environment for archiving or further analysis, as discussed in detail above. As shown at block 210, the method 200 includes analyzing the plurality of image to identify the position of the microscopic beads in a series of consecutive frames. For example, the location of the center of a microscopic bead can be identified to a pixel level or a sub-pixel level accuracy. As shown at block 212, the change in position of each of the microscopic beads is calculated to determine any shift in position of microscopic beads and calculate their distribution. In some embodiments, it can be determined whether the bead position shift distribution obeys a Gaussian distribution having a distribution width that would be expected from the diffusion of free microscopic beads of the size and material of the microscopic beads used. The diffusion coefficient of the microscopic beads can be calculated by calculating the width of the Gaussian distribution. In accordance with the disclosure, a diffusion coefficient of the microscopic beads can also be calculated by injection of the microscopic beads into a solution without genetic material and performing the steps described herein. As shown at decision block 214, the method 200 includes a determination of whether the microscopic beads display Brownian motion. If the microscopic beads do not display Brownian motion, the method proceeds to block 216 and generates a positive output message indicating the presence of the target sequence in the sample under investigation. If the microscopic beads display Brownian motion, the method 200 can optionally proceed to block 218 and generate a negative output message indicating the absence of the target sequence in the sample under investigation.

In accordance with the disclosure, any known method of isolating DNA or RNA from a sample under investigation can be used. For instance, viral RNA/DNA can be extracted from the blood or saliva of a patient or from a food sample after doing the recommended preparation using commercially available RNA/DNA extraction kits. As discussed in embodiments, the extracted RNA/DNA is to detect the presence of specific RNA or DNA by the tethering the DNA/RNA forms with the specially prepared beads.

In some embodiments, the portable video capture device includes a video camera. Many smart phones (and tablets) available today in the market have a good camera with video recording capabilities. In some embodiments, the portable video capture device includes a lens adapter for the video camera. For example, a lens adapter can be used because minimum-focusable distance and the magnification achievable at that distance of a given device might not be adequate to detect the presence of micron to submicron beads in a solution. A lens adapter can be used for video cameras that do not have adequate magnification and resolution to improve the magnification and resolution to enhance bead detection. It is noted that newer phones or electronic communication devices may be designed with camera technology that has higher magnification and resolution, and some embodiments may not require a lens adapter. Lens adapters that can be used in accordance with the disclosure can have, for example, a short focal length and high numerical aperture that can result in magnification in the range of 100-200 times (100-200×) and a spatial resolution of 1 to 2 micrometers. Such characteristics can be achieved, for instance, by a ball-lens based adapter, and it can be attached to and/or placed in front of a video camera of a smart phone.

In some embodiments, the video capture device includes a sample holder. The sample holder can be any device that holds the sample solution in a fixed position relative to the video capture device.

In some embodiments, the video capture device includes a microscopic bead injector. The microscopic bead injector can, for example, be used to add a solution containing microscopic beads containing a DNA probe sequence to a genetic material sample.

In some embodiments, the video capture device includes a portable display. For example, the portable display can include a LCD or LED display. The portable display can be the display of a smart phone, tablet, or smart watch.

The video capture device can include a processor. In some embodiments, the processor is included in a tablet, a smart phone, or smart watch. In some embodiments, the processor is located in a network or in a cloud computing environment. In some embodiments, the processor is distributed. In some embodiments, the processor is not distributed.

In some embodiments, the method includes sending a data collection to a shared pool of configurable computing resources. For example, the method can include sending the plurality of images of the sample, the change in position of each of the microscopic beads, or the determination whether the plurality of beads are displaying Brownian motion for analysis, storage, or archival purposes.

In some embodiments, upon a determination that the plurality of microscopic beads are displaying Brownian motion, and thus that the target sequence is not present in a sample, the method can be repeated with another solution of microscopic beads to detect a different target DNA in the sample. Prior to repeating the method with another solution of microscopic beads either a new microfluidic sample cell can be used or the same sample cell can be flushed with a cleaning solution, such as a clean buffer solution.

Figure 5:
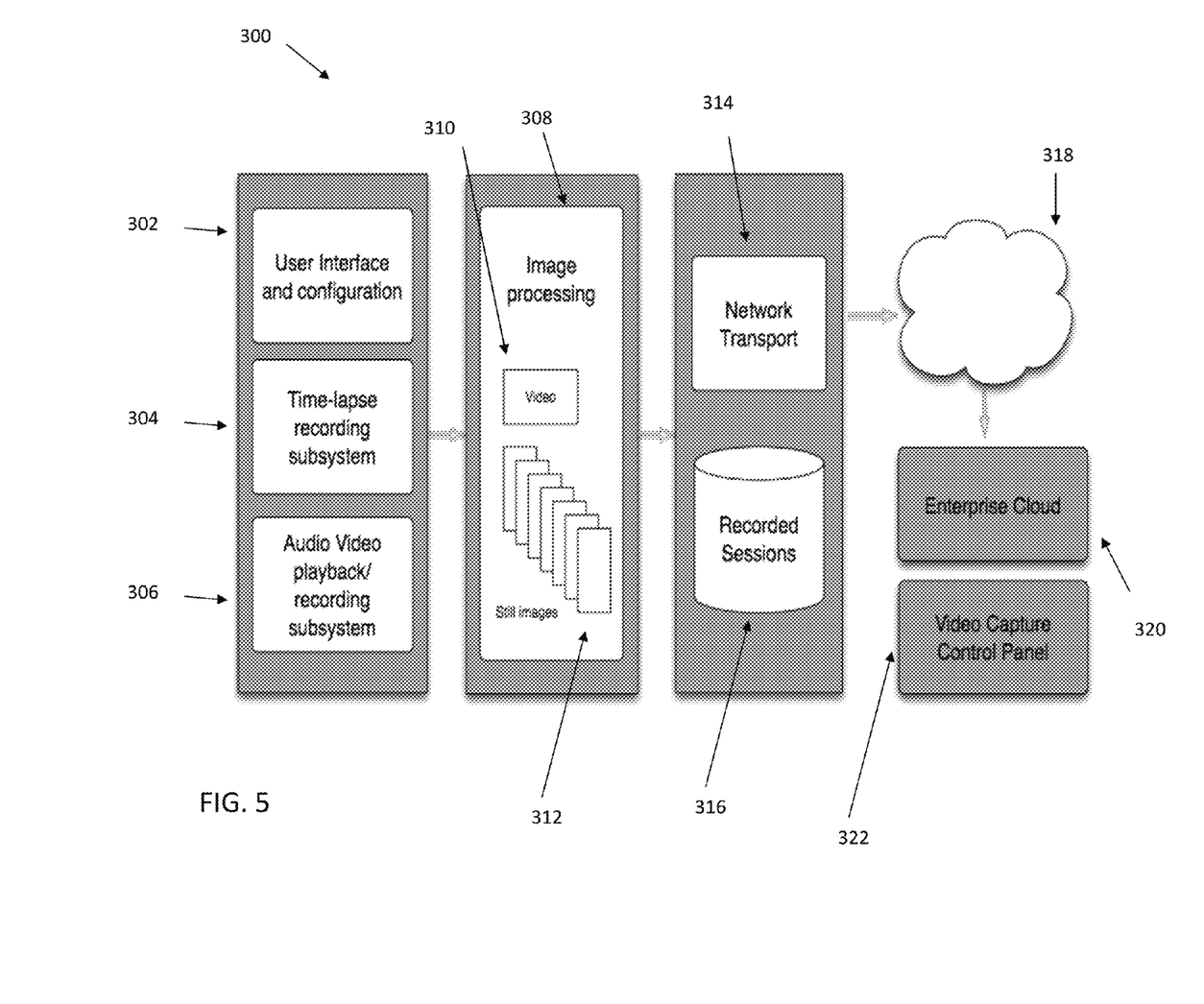
FIG. 5 is a system architecture for communicating the presence of a target DNA or RNA sequence according to one or more embodiments.

FIG. 5 depicts a system architecture 300 for communicating the presence of a DNA or RNA sequence according to one or more embodiments. The system architecture 300 includes a user interface and configuration module 302, a time-lapse recording subsystem 304 and an audio video playback and/or recording subsystem 306, which can be located, for example in a portable device such as a smartphone. The user interface and configuration module 302, a time-lapse recording subsystem 304 and an audio video playback and/or recording subsystem 306 are in communication with an image processing module 308. The image processing module 308 processes video 310 and can generate a plurality of still images 312 from the video 310. The image processing module 308 is in communication with a network transport 314 and a memory module 316 for storing recorded sessions. The network transport 314 can interface with cloud computing environments 318, which can include an enterprise cloud 320. The system architecture 300 also includes a video capture control panel 322.

Figure 6:
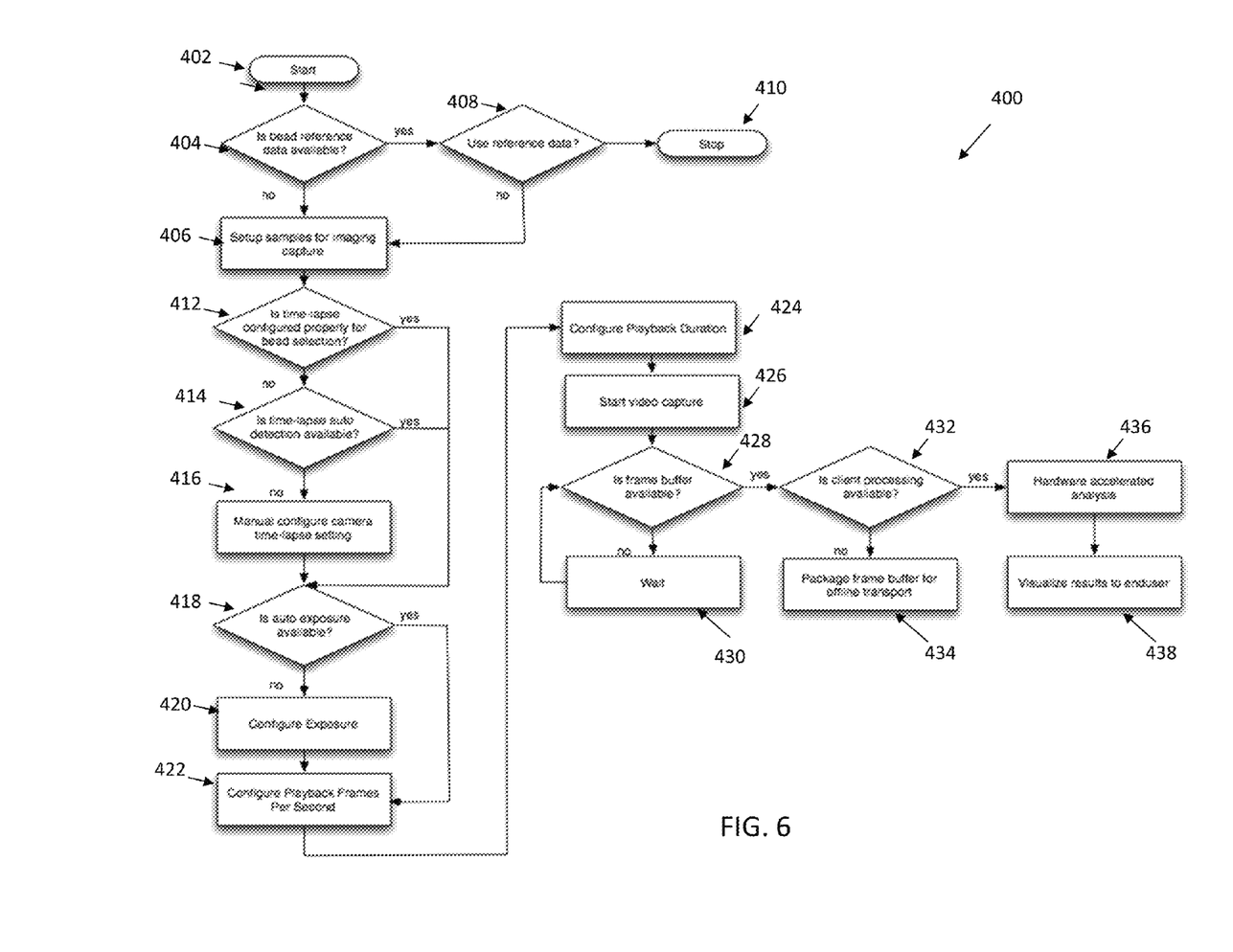
FIG. 6 is a flow diagram illustrating a method for determining bead motion according to one or more embodiments.

FIG. 6 depicts a flow diagram illustrating a method for determining bead motion 400 according to one or more embodiments. The method 400 starts at block 402 and then proceeds to decision block 404 for a determination of whether bead reference data is available. If bead reference data is available, the method 400 asks, as shown at block 408 whether to use the reference data. If reference data is used, the method can stop as shown at block 410. If bead reference data is not available at decision block 404, or if it is determine not to use reference data at block 408, the method 400 proceeds to block 406 and conducts a setup of samples for image capture. Next, as shown at decision block 412, the method asks whether time lapse is configured properly for bead selection. If the answer is no, the method 400 proceeds to decision block 414 and asks whether time-lapse auto detection is available. If the answer is no, the method 400 proceeds to block 416 and manually configures the camera time-lapse setting. If the time-lapse is configured properly for bead selection, as shown block 412, or if time lapse-auto detection is available as shown at block 414, or if the method has manually configured the camera time-lapse setting at block 416, the method proceeds to decision block 418 to determine whether auto exposure is available. If auto exposure is not available, the method 400 includes configuring the exposure as shown at block 420 and then proceeds to configure playback frames per second as shown at block 422. If auto exposure is available, the method proceeds from block 418 to block 422 to configure the playback frames per second. Next, as shown at block 424, playback duration is configured. Then, as shown at block 426, video capture is started. Then, at decision block 428, the method 400 asks whether frame buffer is available. If frame buffer is not available, the method proceeds to block 430 to wait, and then back to decision block 428. If frame buffer is available, the method 400 proceeds to decision block 432 and determines whether client processing is available. If client processing is not available, the method proceeds to block 434 and packages the frame buffer for offline transport. If client processing is available, the method 400 proceeds to block 436 for hardware accelerated analysis. Then, as shown at block 438, the method 400 includes visualizing the results to the end user.

Thus, it can be seen from the forgoing detailed description that one or more embodiments of the present disclosure provide technical effects and benefits. The present disclosure provides communication of the presence of a target DNA or RNA sequence to a user of a portable device. For instance, in one or more embodiments, one can use a smartphone to determine the presence or absence of pathogens or allergens without the need for expensive and cumbersome equipment.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting-data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for communicating the presence of a target DNA or RNA sequence, the method comprising:
    configuring, by a processor, a time-lapse recording system of a portable video capture device for selection of a plurality microscopic beads coated with a DNA probe sequence viewed through a ball-lens adapter;
    configuring, by the processor, an exposure of the time lapse recording system;
    configure, by the processor, a playback frame per second setting of the time lapse recording system;
    receiving, by a processor, a plurality of time-lapse images of a sample solution taken by the time lapse-recording system, wherein each of the images is an image of the sample solution at a unique time, and wherein the sample solution comprises the plurality of microscopic beads coated with the DNA probe sequence and a genetic material sample;
    calculating, by the processor, a change in position of each of the microscopic beads coated with the DNA probe sequence over time based upon the plurality of time-lapse images;
    determining, based at least in part upon the calculated changes in position, whether the plurality of microscopic beads are displaying Brownian motion;
    responsive to a determination that the plurality of microscopic beads are displaying Brownian motion, generating a negative output message and sending the negative output message to a portable display; and
    responsive to a determination that the plurality of microscopic beads are not displaying Brownian motion, generating a positive output message and sending the positive output message to the portable display.

2. The computer-implemented method of claim 1, wherein the portable video capture device comprises:
    a video camera;
    a time-lapse recording subsystem;
    an audio video playback subsystem;
    an image processing module capable of generating a plurality of still images from a video;
    a network transport in communication with the image processing module;
    a memory module for storing video recordings;
    a lens adapter for the video camera;
    a sample holder;
    a microscopic bead injector; and
    the portable display.

3. The computer-implemented method of claim 1, wherein the portable video capture device is a tablet, a smart phone or a smart watch.

4. The computer-implemented method of claim 1, wherein the method further comprises calculating a diffusion coefficient of the DNA probe sequence.

5. The computer-implemented method of claim 1, wherein the processor is in a distributed network.

6. The computer-implemented method of claim 1, wherein the positive output message comprises an indication that a target DNA or RNA sequence corresponding to the DNA probe is present in the sample solution.

7. The computer-implemented method of claim 1, the method further comprising sending a data collection to a shared pool of configurable computing resources.

8. The computer-implemented method of claim 7, wherein the data collection comprises the plurality of images of the sample, the change in position of each of the microscopic beads, or the determination whether the plurality of beads are displaying Brownian motion.

9. A computer program product for communicating the presence of a target DNA or RNA sequence, the computer program product comprising:
a non-transitory storage medium readable by a processing circuit and storing instructions for execution by the processing circuit for performing a method comprising:
configuring a time-lapse recording system of a portable video capture device for selection of a plurality of microscopic beads coated with a DNA probe sequence viewed through a ball lens adapter;
configuring an exposure of the time lapse recording system;
configuring a playback frame per second setting of the time lapse recording system;
receiving a plurality of time-lapse images of a sample solution taken by the time-lapse recording system, wherein each of the images is an image of the sample solution at a unique time, and wherein the sample solution comprises the plurality of microscopic beads coated with the DNA probe sequence and a genetic material sample;
calculating a change in position of each of the microscopic beads coated with the DNA probe sequence over time based upon the plurality of time-lapse images;
determining, based upon the calculated changes in position, whether the plurality of microscopic beads are displaying Brownian motion;
responsive to a determination that the plurality of microscopic beads are displaying Brownian motion, generating a negative output message and sending the negative output message to a portable display; and
responsive to a determination that the plurality of microscopic beads are not displaying Brownian motion, generating a positive output message and sending the positive output message to the portable display.

10. The computer program product of claim 9, wherein the portable video capture device comprises:
a video camera;
a time-lapse recording subsystem;
an audio video playback subsystem;
an image processing module capable of generating a plurality of still images from a video;
a network transport in communication with the image processing module;
a memory module for storing video recordings;
a lens adapter for the video camera;
a sample holder; and
a microscopic bead injector.

11. The computer program product of claim 9, wherein portable video capture device is a tablet, a smart phone, or a smart watch.

12. The computer program product of claim 9, wherein the processor is further configured to calculate a diffusion coefficient of the DNA probe sequence.

13. The computer program product of claim 9, wherein the negative output message comprises an indication that a target DNA or RNA sequence corresponding to the DNA probe is not present in the sample solution.

14. The computer program product of claim 9, wherein the positive output message comprises an indication that a target DNA or RNA sequence corresponding to the DNA probe is present in the sample solution.

15. The computer program product of claim 9, wherein the processor is further configured to send a data collection to a shared pool of configurable computing resources.

16. A processing system for communicating the presence of a target DNA or RNA sequence, comprising:
a portable video capture device comprising a time-lapse recording system and a ball lens adapter;
a portable display; and
a processor in communication with one or more types of memory, the processor configured to:
configure the time-lapse recording system of the portable video capture device for selection of a plurality of microscopic beads coated with a DNA probe sequence viewed through the ball lens adapter;
configure an exposure of the time lapse recording system;
configure a playback frame per second setting of the time lapse recording system;
receive a plurality of time-lapse images of a sample solution taken by the time-lapse recording system, wherein each of the images is an image of the sample solution at a unique time, and wherein the sample solution comprises the plurality of microscopic beads coated with the DNA probe sequence and a genetic material sample;
calculate a change in position of each of the microscopic beads coated with the DNA probe sequence over time based upon the plurality of time-lapse images;
determine, based upon the calculated changes in position, whether the plurality of microscopic beads are displaying Brownian motion;
responsive to a determination that the plurality of microscopic beads are displaying Brownian motion, generate a negative output message and send the negative output message to the portable display; and
responsive to a determination that the plurality of microscopic beads are not displaying Brownian motion, generate a positive output message and send the positive output message to the portable display.

17. The processing system of claim 16, wherein the portable video capture device comprises:
a video camera;
a time-lapse recording subsystem;
an audio video playback subsystem;
an image processing module capable of generating a plurality of still images from a video;
a network transport in communication with the image processing module;
a memory module for storing video recordings;
a lens adapter for the video camera;
a sample holder; and
a microscopic bead injector.

18. The processing system of claim 16, wherein the portable video capture device is a tablet, a smart phone, or a smart watch.

19. The processing system of claim 16, wherein the processor is further configured to send a data collection to a shared pool of configurable computing resources.

20. The processing system of claim 16, wherein the positive output message comprises an indication that a target DNA or RNA sequence corresponding to the DNA probe is present in the sample solution.

* * * * *